US00PP15853P2

(12) United States Plant Patent
Olesen et al.

(10) Patent No.: US PP15,853 P2
(45) Date of Patent: Jul. 12, 2005

(54) MINIATURE ROSE PLANT NAMED 'POULHI021'

(50) Latin Name: *Rosa hybrida*
Varietal Denomination: POULhi021

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 33 days.

(21) Appl. No.: 10/787,275

(22) Filed: Feb. 27, 2004

(51) Int. Cl.[7] ..... A01H 5/00
(52) U.S. Cl. ..... Plt./122
(58) Field of Search ..... Plt./122

(56) References Cited

U.S. PATENT DOCUMENTS

PP13,170 P2 * 11/2002 Olesen et al. ..... Plt./122
PP14,798 P3 * 5/2004 Olesen et al. ..... Plt./122

OTHER PUBLICATIONS

UPOV ROM GTITM Computer Database, GTI Jouve Retrieval Software 2004/04 Citation for 'POULhi021'.*

* cited by examiner

*Primary Examiner*—Kent Bell
*Assistant Examiner*—W. C. Haas

(57) ABSTRACT

A new miniature rose plant which has abundant, red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULhi021'.

SUMMARY OF THE INVENTION

The present discovery constitutes a new and distinct variety of a miniature pot rose plant which was discovered in a cultivated area. The mutation resulted from 'Poulhi005', a miniature pot rose hybridized by the same inventors. 'Poulhi005' is described and illustrated in (U.S. Plant Pat. No. 14,798). The new rose variety resulted from a naturally occurring mutation of unknown causation on a branch of 'Poulhi005'.

The rose plant of the present discovery has the following unique combination of characteristics which are outstanding in the new variety and which distinguish it from the original rose 'Poulhi005'.

1. Whereas 'Poulhi005' has a petal count of 32 to 34, 'POULhi021' has over 43 petals.
2. Whereas 'Poulhi005' has an upper surface petal color of Red Group 44B, the same of 'Poulhi021' is Red Group 42A to Red Group 53B.

This combination of qualities is not present in previously available commercial cultivars of this type, known to the inventors, and distinguish 'POULhi021' from all other varieties of which we are aware. For example, 'POULhi021' has:

1. Uniform and abundant red flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

The resulting mutation was selected and evaluations were conducted on the resulting rose plants in a controlled environment.

Asexual reproduction of 'POULhi021' by cuttings and traditional budding was first done by L. Pernille and Mogens N. Olesen in their nursery in Fredensborg, Denmark in 1998. This initial and other subsequent propagations conducted in controlled environments have demonstrated that the characteristics of 'POULhi021' are stable and reproduced true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'POULhi021'. Specifically illustrated in the drawing:

FIG. 1.1; Open flower and stem showing open flower, branching and the attachment of leaves, buds, and peduncles;

FIG. 1.2; Flower bud closed, partially open, and open;

FIG. 1.3; Flower petals, detached;

FIG. 1.4; Sepals, receptacle, and pedicel;

FIG. 1.5; Juvenile leaves exhibiting anthocyanin at leaf margins and mature leaves;

FIG. 1.6; Bare stem.

DETAILED DESCRIPTION OF THE VARIETY

The following is a description of 'POULhi021', as observed in its growth in glasshouses in Fredensborg, Denmark. Color references are made using The Royal Horticultural Society (London, England) Colour Chart, 1995, except where common terms of color are used.

For a comparison, several physical characteristics of the rose variety 'POULra007', (U.S. Plant Pat. No. 13,710) are compared to 'POULhi021' in Chart 1.

CHART 1

| | 'POULhi021' | 'POULra007' |
|---|---|---|
| Petalage | 43 petals with 15 petaloids | 40–50 petals with 0–5 petaloids |
| After flower opening, color of outer petals, upper surface | Red Group 42A to Red Group 53B | Red Group 45B |
| Typical leaf size | 115 mm (l) × 80 mm (w) | 60–70 mm (l) × 45–50 mm (w) |

FLOWER AND FLOWER BUD

Blooming habit: Continuous.

Flower bud:

*Size.*—Upon opening, 27 mm in length from base of receptacle to end of bud. Diameter of flower bud is 11 mm.

*Bud form.*—Pointed ovoid.

*Bud color.*—As sepals unfold, Red Group 53B; Red Group 53B at ¼ opening.

*Sepals.*—Upper surface: Color: Yellow-Green Group 144A to Green Group 138B. Texture: Slightly pubescent. Lower surface: Color: Yellow-Green Group 144A. Shape: Sepal apex is cirrhose. Base is flat at union with receptacle. Margins: Margins have weak foliaceous appendages on three of the five sepals. Abundant stipitate glands are very fragrant, somewhat pine scented. Size: 33 mm (l)×8 mm (w).

*Receptacle.*—Surface: Smooth. Shape: Urn-shaped. Size: 8 mm (h)×5 mm (w). Color: Yellow-Green Group 144B.

*Peduncle.*—Surface: Stipitate glands are abundant. Length: 20 to 40 mm. Color: Yellow-Green Group 144B. Strength: Strong.

*Borne.*—Multiples of 1 to 4 buds per flowering stem.

Flower bloom:

*Fragrance.*—Light floral scent.

*Duration.*—The blooms have a duration on the plant of approximately 21 days. Petals fall cleanly away from plant.

*Size.*—12–15 cm pot rose. Average flower diameter is 50 to 55 mm when open. Flower depth is typically 22 mm.

*Form.*—Imbricated. General shape is an open cup with reflexing flower petals.

*Shape of flower when viewed from the side.*—Upon opening, upper part: Flat. Upon opening, lower part: Flat. Open flower, upper part: Flat. Open flower, lower part: Convex.

*Petalage.*—On average 43 petals under normal conditions with 15 petaloids.

Color:

*Upon opening, petals.*—Outermost petals: Outer side: Red Group 45B. Inner side: Red Group 42A to Red Group 53B. Innermost petals: Outer side: Red Group 45B. Inner side: Red Group 42A to Red Group 53B.

*Upon opening, basal petal spots.*—Outermost petals: Outer side: White Group 155C. Inner side: White Group 155C. Innermost petals: Outer side: White Group 155C. Inner side: White Group 155C.

*After opening, petals.*—Outermost petals: Outer side: Red Group 45B to 45C. Inner side: Red Group 42A to Red Group 53B. Innermost petals: Outer side: Red Group 45B. Inner side: Red Group 42A to Red Group 53B.

*After opening, basal petal spots.*—Outermost petals: Outer side: White Group 155C. Inner side: White Group 155C. Innermost petals: Outer side: White Group 155C. Inner side: White Group 155C.

General tonality: On open flower Red Group 42A to Red Group 53B. No change in the general tonality at the end of the $10^{th}$ day.

Petals:

*Petal reflex.*—Strongly.

*Petal margin.*—Entire. With medium undulations.

*Shape.*—Base: Acute to round. Apex: Round with point at apex.

*Size.*—25 mm (l)×22 mm (w).

*Thickness.*—Thick.

*Texture.*—Smooth.

*Arrangement.*—Not formal.

Petaloids:

*Quantity.*—15 to 25.

*Size.*—11 mm (l)×12 mm (w).

*Shape.*—Irregular and rounded.

*Color.*—Red Group 45B.

Reproductive organs:

*Pistils.*—Length: 10 mm. Quantity: 45 (actual count).

*Pollen.*—None observed.

*Anthers.*—Size: 3 mm long. Color: Greyed-Yellow Group 160B. Quantity: 35 (actual count).

*Filaments.*—Color: Yellow-Green Group 150D. Length: 3 mm.

*Stigmas.*—Superior relative to the length of the filaments and the height of the anthers. Color: Yellow-Green Group 145B to 145C.

*Styles.*—Color: Yellow-Green Group 145B to 145C.

*Seed formation.*—Not observed.

PLANT

Plant growth: Vigorous, compact, upright to bushy. When grown as a 12–15 cm pot plant, the average height of the plant itself is 22 cm and the average width is 14 cm.

Stems:

*Color.*—Young wood: Yellow-Green Group 144B. Older wood: Yellow-Green Group 144B.

*Internodal distance.*—23 mm (average).

*Length of stems.*—14 cm.

*Surface texture.*—Young wood: Smooth. Older wood: Smooth.

Thorns:

*Incidence.*—2 mm per 10 cm of stem.

*Size.*—Average length is 3 mm.

*Color.*—Greyed-Orange Group 163C.

*Shape.*—Linear.

Plant foliage: Normal number of leaflets on normal leaves in middle of the stem: 5 leaflets.

*Compound leaf size.*—115 mm (l)×80 mm (w).

*Color.*—Juvenile foliage: Upper surface: Green Group 137A. Lower surface: Yellow-Green Group 147C. Mature foliage: Upper surface: Green Group 137A. Lower surface: Yellow-Green Group 147C.

Plant leaves and leaflets:

*Stipules.*—Size: 12 mm in length. Margins: Finely serrated with abundant stipitate glands. Color: Green Group 137C.

*Petiole.*—Length: 20 mm. Color: Above: Yellow-Green Group 146A. Underneath: Yellow-Green Group 146C. Anthocyanin: Greyed-Orange Group 176A. Surface: Thorns and stipitate glands.

*Rachis.*—Size: 30 mm. Color: Above: Yellow-Green Group 146A. Underneath: Yellow-Green Group 146C. Anthocyanin: Greyed-Orange Group 176A. Surface: Thorns and stipitate glands observed.

*Leaflet.*—Size: 55 mm (l)×25 mm (w). Edge: Serrated. General shape: Lanceolate. Apex shape: Acute. Base shape: Attenuate. Texture: Smooth. Arrangement: Odd pinnate. Venation: Reticulate. Glossiness: Moderately glossy. Thickness: Medium.

Disease resistance: Above average resistance to mildew, black spot, and *Botrytis* under normal growing conditions in Fredensborg, Denmark.

It is claimed:

1. A new and distinct variety of rose plant of the miniature class, substantially as herein illustrated and described as a distinct and novel rose variety due to its abundant, red flowers, vigorous growth, compact habit, suitability for production from softwood cuttings in pots, and exceptionally durable flowers and foliage which make the variety suitable for distribution in the floral industry.

* * * * *

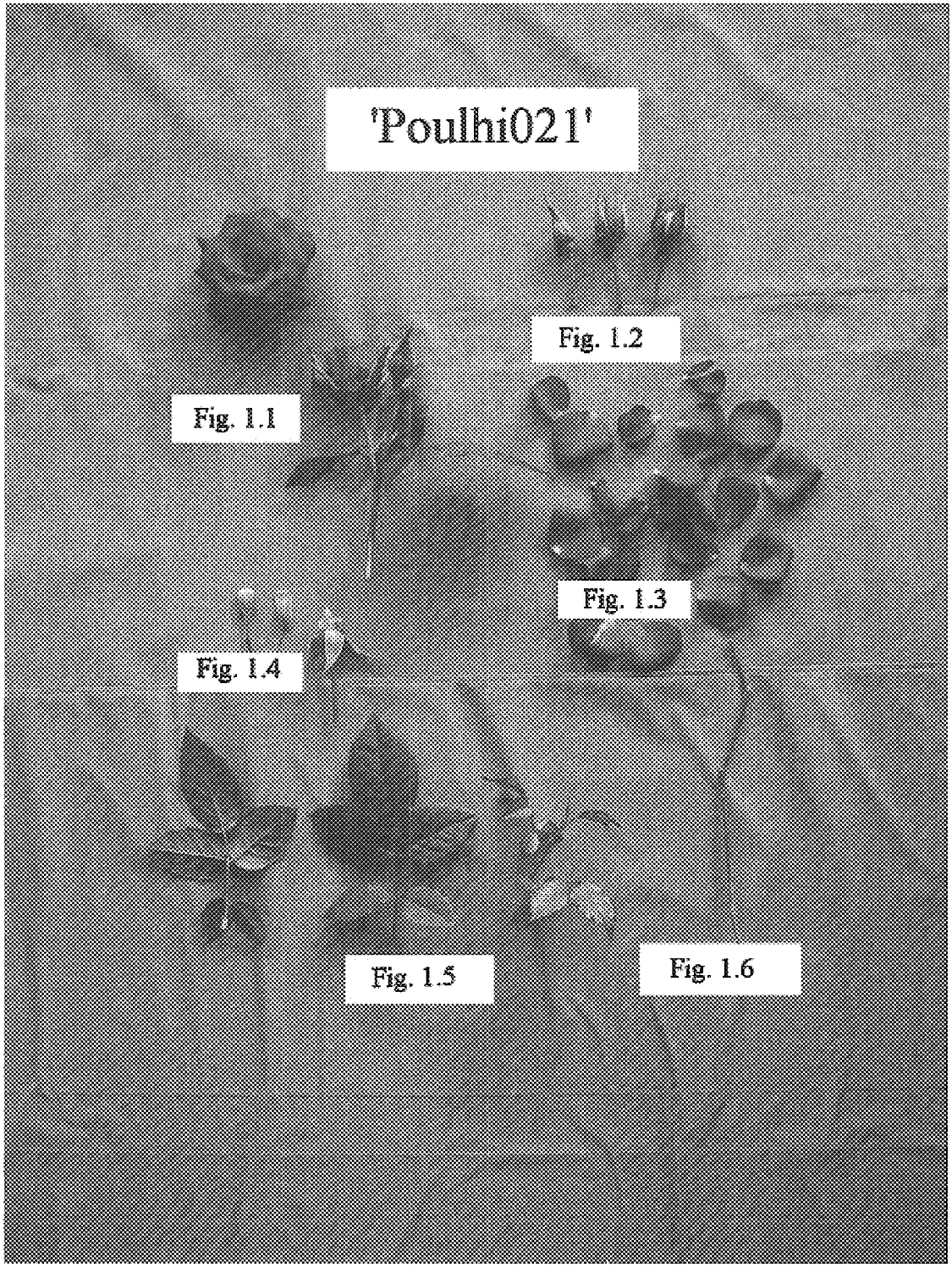
'Poulhi021'
Fig. 1.1
Fig. 1.2
Fig. 1.3
Fig. 1.4
Fig. 1.5
Fig. 1.6